United States Patent [19]
Labat et al.

[11] Patent Number: 5,095,138
[45] Date of Patent: Mar. 10, 1992

[54] CONTINUOUS SYNTHESIS OF MERCAPTOCARBOXYLIC ACID ESTERS

[75] Inventors: Yves Labat; Jean-Pierre Muller, both of Pau; Daniel Litvine, Lescar, all of France

[73] Assignee: Societe Nationale Elf Aquitaine (Production), Courbevoie, France

[21] Appl. No.: 593,137

[22] Filed: Oct. 5, 1990

[30] Foreign Application Priority Data

Oct. 6, 1989 [FR] France .................. 89 13102

[51] Int. Cl.$^5$ .................................. C07C 319/12
[52] U.S. Cl. ........................ 560/147; 562/512
[58] Field of Search ................ 560/147; 562/512

[56] References Cited
U.S. PATENT DOCUMENTS 3,954,843  5/1976  Helmlinger et al. .......... 560/147

FOREIGN PATENT DOCUMENTS 1056193  1/1967  United Kingdom .

Primary Examiner—Jose G. Dees
Assistant Examiner—Vera C. Clarke
Attorney, Agent, or Firm—Morgan & Finnegan

[57] ABSTRACT

The invention relates to production of esters of mercaptocarboxylic acids and alcohols forming an azeotrope with water.

The esterification is carried out continuously in the presence of an excess of alcohol and the water formed is removed by entraining azeotropically under vacuum at a temperature such that the residual water concentration in the reaction mixture remains constantly below 0.5% by weight.

The process according to the invention applies more particularly to the synthesis of octyl esters of thioglycolic acid.

9 Claims, No Drawings

CONTINUOUS SYNTHESIS OF MERCAPTOCARBOXYLIC ACID ESTERS

FIELD OF THE INVENTION

The present invention relates to the production of mercaptocarboxylic acid esters and more particularly to that of the octyl esters of thioglycolic acid.

BACKGROUND OF THE INVENTION

The significant development of these esters for the preparation of tin stabilizers of chlorovinyl polymers makes their continuous production and the improvement of the synthesis yield highly desirable. On the other hand, the quality of the stabilizers largely depends on that of the esters, in particular their purity and their stability on storage.

Although it appears easy to esterify an alcohol forming an azeotrope with water, such as 2-ethylhexanol or mixtures of isomers of $C_8$ alcohols (isooctanol), using an organic acid stable to heat, it is no longer the same for a mercaptocarboxylic acid which is unstable to heat, such as thioglycolic acid. In fact, by dehydration, this acid forms an esterifiable oligomer leading to the production of undesirable by-products in accordance with the equation:

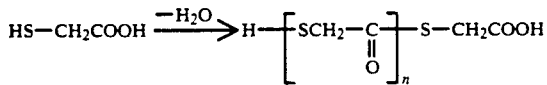

wherein n is predominantly equal to 1 (dimer) but can also be more than 1. It is also known that this straight-chain dimer can easily esterify in accordance with the equation:

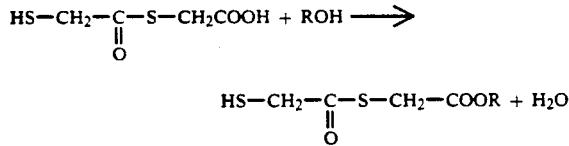

Thus, the esterification of a mercaptocarboxylic acid such as thioglycolic acid involves several competitive reactions which, depending on the operating conditions used, can cause more or less significant formation of undesirable by-products. In discontinuous operation, preventing the formation of esterified dimers and, at the same time, obtaining a high conversion of mercaptocarboxylic acid is not successful.

It has now been found that the selectivity for the desired ester can be substantially improved if the esterification is carried out continuously, regularly removing the water formed in such a way that the residual water concentration in the reaction mixture is below 0.5% by weight. It has also been found, surprisingly, that, under these conditions, the reaction time is clearly shorter than that of the discontinuous process.

DETAILED DESCRIPTION OF THE INVENTION

The subject of the invention is, therefore, a process for the production of esters of mercaptocarboxylic acids and alcohols forming an azeotrope with water, characterized in that the esterification is carried out continuously in the presence of an excess of alcohol(s) and in that the water formed is removed as fast as it is formed, by entraining azeotropically under vacuum at a temperature such that the residual water concentration in the reaction mixture remains constantly below 0.5% by weight, preferably equal to or below 0.1% and advantageously below 0.05%.

The process according to the invention can be carried out in a single reactor. However, it is preferred to operate in two successive reactors (in series), the first operating at a residual water concentration of between 0.2 and 0.5% and the second at a residual water concentration below 0.1% and preferably below 0.05%.

The feed of alcohol and mercaptocarboxylic acid to the single reactor or to the first reactor in the case where two reactors are used in series must be controlled in such a way that the molar ratio of alcohol/mercaptocarboxylic acid is between 1.1 and 1.4. The alcohol entrained with the water is separated from the water by decanting and recycled to the reactor.

The esterification catalyst used is preferably sulphuric acid, but it is also possible to use other known esterification catalysts such as, for example, methanesulphonic acid, benzenesulphonic acid or p-toluenesulphonic acid. The amount of catalyst to be used can vary within wide limits without influencing the selectivity; it is generally between about 0.25 and 12.5 millimoles per mole of mercaptocarboxylic acid and preferably between 1.25 and 5 millimoles.

The pressure in the reactor or reactors is controlled to obtain satisfactory removal of the water formed. It depends not only on the value chosen for the residual water concentration but also on the temperature of the reaction mixture, a lower temperature necessitating a lower pressure.

The temperature at which the esterification according to the invention is carried out can vary within wide limits as a function of the residual water concentration chosen, the pressure applied and the nature of the alcohol used. In general, the temperature is advantageously between about 80° and 140° C. For 2-ethylhexanol and isooctanol, the reaction is preferably carried out at a temperature on the order of 120°-130° C.

The residual water concentration of the reaction mixture can be monitored in a known manner, for example by infrared determination.

The residence time of the reactants in the reactor(s) can vary within wide limits. It is advantageously between 10 and 150 minutes and preferably between about 30 and 80 minutes.

Although the process according to the invention has as its aim more particularly the synthesis of octyl esters of thioglycolic acid, it can also be applied to the production of esters derived from other mercaptocarboxylic acids, such as, for example, thiolactic acid or 3-mercaptopropionic acid, and/or derived from other $C_2$ to $C_{18}$ aliphatic or cycloaliphatic alcohols, preferably $C_4$ to $C_{12}$ alcohols, such as, for example, butanol, hexanol, cyclohexanol, decanol and dodecanol.

EXAMPLES

The following examples illustrate the invention without restricting it. The abbreviations used have the following meanings:

| | |
|---|---|
| TGA: | thioglycolic acid: HS—CH$_2$—COOH |
| EHTG: | 2-ethylhexyl thioglycolate: |

| | |
|---|---|
| DIM: | HS—CH$_2$—COO—CH$_2$CH(C$_2$H$_5$)—(CH$_2$)$_3$—CH$_3$ dimer of TGA: HS—CH$_2$—CO—S—CH$_2$—COOH |
| EDM: | 2-ethylhexyl ester of the dimer of TGA: HS—CH$_2$—CO—S—CH$_2$—COO—CH$_2$CH(C$_2$H$_5$)—(CH$_2$)$_3$—CH$_3$ |
| EDS: | 2-ethylhexyl dithiodiglycolate: C$_8$H$_{17}$—OCO—CH$_2$—S—S—CH$_2$—COO—C$_8$H$_{17}$ |

EXAMPLE 1

A stirred glass reactor having a volume of 1.5 liters and a height/diameter ratio of 3.5, thermostat-controlled by a double wall and provided with conventional means for regulating the vacuum and the level is used. It is connected to a vacuum pump via a condenser to separate the water/alcohol azeotrope. The alcohol is recycled to the reactor.

This reactor is fed continuously with 1250 g/hour of a mixture containing, by weight, 35% of TGA, 0.1% of DIM, 64.8% of 2-ethylhexanol and 0.1% of H$_2$SO$_4$.

After a stage of establishing usual operation enabling equilibrium of the operating parameters to the following values to be obtained:

residence time: 55 minutes
temperature: 130° C.
pressure: 25.33 kPa (190 torr)
acid number (AN): 8.6 mgKOH/g 81.4 g/hour of an aqueous phase containing 0.44% of TGA are collected in the condenser and 1160 g/hour of a mixture are withdrawn continuously, the analysis of which mixture by acidimetry (TGA), by NMR (all of the organic constituents) and by IR (water) enables the following composition to be determined:

| | % by weight |
|---|---|
| TGA | 1.4 |
| Ethylhexanol | 17.45 |
| EHTG | 80.6 |
| EDM | 0.2 |
| EDS | 0.1 |
| Water | 0.25 | which corresponds to a degree of conversion of TGA of 96% and to a selectivity for EHTG of about 99.4%.

EXAMPLES 2 TO 5

The procedure is as in Example 1 except that at least one of the operating parameters (residence time, temperature, pressure) is modified.

The operating conditions and the results thus obtained are collated, with those of Example 1, in the following table.

TABLE 1

| | EXAMPLE | | | | |
|---|---|---|---|---|---|
| | 1 | 2 | 3 | 4 | 5 |
| OPERATING CONDITIONS | | | | | |
| residence time (mn) | 55 | 140 | 80 | 55 | 60 |
| temperature (°C.) | 130 | 130 | 130 | 120 | 130 |
| pressure (kPa) | 25.33 | 50.66 | 22 | 13.33 | 26.66 |
| AN (mgKOH/g) | 8.6 | 9.4 | 5.8 | 8 | 7.5 |
| residual water (%) | 0.25 | 0.3 | 0.2 | 0.25 | 0.23 |
| RESULTS | | | | | |
| Molar composition of the product withdrawn (%): | | | | | |
| EHTG | 74.4 | 72 | 74.2 | 75.1 | 78.0 |
| EDM | 0.15 | 0.1 | 0.16 | 0.2 | 0.2 |
| ethylhexanol | 25 | 25.3 | 24.9 | 24.1 | 21 |
| Conversion of TGA (%) | 96 | 95.6 | 97 | 96 | 96 |
| Selectivity for EHTG (%) | 99.4 | 99.4 | 99.4 | 99.4 | 99.3 |

COMPARATIVE EXAMPLE 6 (Discontinuous experiments)

1,600 g of a mixture containing approximately, by weight, 39.4% of TGA 0.1% of DIM, 60.4% of 2-ethylhexanol and 0.1% of H$_2$SO$_4$ is introduced into a 2-liter stirred and thermostat-controlled reactor. The mixture is then heated to 110°–130° C. under vacuum, the initial pressure of 100 kPa falling to 2.66 kPa after 7 hours.

At the end of this time, the reaction mixture has an acid number of 3.7 mgKOH/g and its analysis indicates the following molar composition:

| | |
|---|---|
| EHTG | 88% |
| EDM | 1.09 |
| Ethylhexanol | 10% | which corresponds to a conversion of TGA of 98% and to a selectivity for EHTG of 97.5%.

A second experiment carried out under the same conditions but with a higher molar ratio of ethylhexanol/TGA (1.2 instead of 1.1), that is to say employing 1,600 g of a mixture containing, by weight, 37% of TGA, 0.1% of DIM, 62.8% of 2-ethylhexanol and 0.1% of H$_2$SO$_4$, leads to the following results after a reaction time of 8 hours:

| | |
|---|---|
| AN | 1.6 mgKOH/g |
| EHTG | 77% |
| EDM | 0.7% |
| Ethylhexanol | 22.1% | which corresponds to a conversion of TGA of 99% and to a selectivity for EHTG of 98.2%.

By comparison with Examples 1 to 5 carried out continuously, it is found that the discontinuous mode is much longer and leads to the formation of EDM.

EXAMPLE 7

The reaction is carried out in two reactors identical to that described in Example 1 and arranged in series.

The first reactor operates under exactly the same conditions as in Example 1. The second reactor is fed with the product withdrawn from the first reactor (1,160 g/H) and operates under the following conditions:

| | |
|---|---|
| Residence time: | 40 minutes |
| Temperature: | 130° C. |
| Pressure: | 9.33 kPa |
| Acid Number: | 1.2 mgKOH/g |

Once operating equilibrium has been obtained, 1,145 g/hour of a product having the following composition:

| | % by weight |
|---|---|
| TGA | 0.2 |
| Ethylhexanol | 15.1 |
| EHTG | 84.3 |
| EDM | 0.27 |
| EDS | 0.08 |
| Water | 0.04 | which corresponds to a degree of conversion of TGA of 99.4% and to a selectivity for EHTG of 99.35%, is withdrawn continuously from the second reactor.

EXAMPLE 8

The procedure is carried out as in Example 7 in two reactors in series and replacing 2-ethylhexanol by isooctanol (technical grade mixture of isomers of $C_8$ alcohols).

The following collates the operating conditions and results obtained.

TABLE 2

| | First reactor | Second reactor |
|---|---|---|
| OPERATING CONDITIONS | | |
| residence time (minutes) | 55 | 50 |
| temperature (°C.) | 130 | 130 |
| pressure (kPa) | 26.66 | 13.33 |
| AN (mgKOH/g) | 9.4 | 1.8 |
| residual water (%) | 0.34 | 0.06 |
| RESULTS | | |
| Molar composition of the product withdrawn (%): | | |
| isooctyl thioglycolate | 75.4 | 75.6 |
| isooctyl ester of the DIM | 0.15 | 0.2 |
| isooctanol | 24.5 | 24 |
| Conversion of TGA (%) | 95 | 99 |
| Selectivity for isooctyl thioglycolate (%) | 99.6 | 99.5 |

EXAMPLE 9

The procedure is carried out as in Example 7 in two reactors in series.

The first reactor is fed at a rate of 1160 g/hr of a mixture containing, by weight, 47.6% of TGA, 0.4% of DIM, 51.9% of butanol and 0.1% of $H_2SO_4$, the operating conditions being the following:

Residence time: 60 minutes
Temperature: 73° C.
Pressure: 10 kPa

Once operating equilibrium has been obtained, 80 g/hr of aqueous condensate is eliminated and the product withdrawn is fed to the second reactor which operates under the following conditions:

Residence time: 60 minutes
Temperature: 70° C.
Pressure: 6 kPa

Under equilibrium conditions, a product having the following weight composition:

| TGA | 0.6% |
|---|---|
| Butanol | 15.5% |
| Butyl thioglycolate | 83.7% |
| Water | 0.1% | was withdrawn from the second reactor, which corresponds to a degree of conversion of TGA of 98.5% and a selectivity for butyl thioglycolate greater than 99%.

EXAMPLE 10

The procedure is carried out as in Example 7 in two reactors in series functioning continuously under the following conditions:

| | First Reactor | Second Reactor |
|---|---|---|
| Residence time (minutes) | 60 | 60 |
| Temperature | 130° C. | 140° C. |
| Pressure (kPa) | 26 | 10.6 |

The first reactor is fed with 220 g/hr of a mixture containing, by weight, 25.1% of TGA, 0.2% of DIM, 74.6% of isotridecanol and 0.1% of $H_2SO_4$.

Once operating equilibrium has been obtained, an extract was obtained from the outlet of the second reactor having an acid index of 1.6 mgKOH/g. The conversion of TGA is 99% and the selectivity for isotridecyl thioglycolate is greater than 99%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the production of esters of mercaptocarboxylic acids and alcohols forming an azeotrope with water, by reacting said acid and alcohol continuously fed in a molar ratio of alcohol/acid between 1.1 and 1.4, in the presence of an esterification catalyst and removing water formed as fast as it is formed, by entraining azeotropically under vacuum at a temperature such that residual water concentration in the reaction mixture remains constantly below 0.5% by weight.

2. Process according to claim 1, wherein the residual water concentration is equal to or below 0.1% by weight.

3. Process according to claim 2, wherein the residual water concentration is below 0.05% by weight.

4. Process according to claim 1, wherein the esterification is carried out in two successive reactors, the first reactor operating at a residual water concentration of between 0.2 and 0.5% and the second reactor operating at a residual water concentration below 0.1%.

5. Process according to claim 1, wherein the reaction is carried out at a temperature between about 80° and 140° C.

6. Process according to claim 1, wherein the esterification catalyst is sulphuric acid, methanesulphonic acid, benzenesulphonic acid or p-toluenesulphonic acid.

7. Process according to claim 1, wherein the mercaptocarboxylic acid is thioglycolic acid, thiolactic acid or 3-mercaptopropionic acid.

8. Process according to claim 1, wherein a $C_2$ to $C_{12}$ aliphatic or cycloaliphatic alcohol is used.

9. Process according to claim 1, wherein 2-ethylhexanol or isooctanol is used and the reaction is carried out at a temperature between about 120°–130° C.

* * * * *